(12) United States Patent
Prabhat et al.

(10) Patent No.: US 7,459,550 B2
(45) Date of Patent: Dec. 2, 2008

(54) PROCESS FOR THE PREPARATION OF CEFDITOREN

(75) Inventors: Kumar Sahoo Prabhat, Chennai (IN); Anandam Vempali, Chennai (IN); Sivakumaran Sundaravadivelan, Chennai (IN); Nagesh Ganesh Praveen, Chennai (IN); Manikrao Waghdare Vittal, Chennai (IN); Balawant Deshpande Pandurang, Chennai (IN); Kumar Luthra Parven, Chennai (IN); Ramesh Sathe Pratik, Chennai (IN)

(73) Assignee: Orchid Chemicals & Pharmaceuticals Ltd., Chennai (IN)

( * ) Notice: Subject to any disclaimer, the term of this patent is extended or adjusted under 35 U.S.C. 154(b) by 394 days.

(21) Appl. No.: 10/563,371

(22) PCT Filed: Jul. 3, 2004

(86) PCT No.: PCT/IB2004/002203

§ 371 (c)(1),
(2), (4) Date: Jan. 4, 2006

(87) PCT Pub. No.: WO2005/003141

PCT Pub. Date: Jan. 13, 2005

(65) Prior Publication Data

US 2006/0173175 A1 Aug. 3, 2006

(30) Foreign Application Priority Data

Jul. 4, 2003 (IN) .......................... 555/CHE/2003

(51) Int. Cl.
C07D 501/24 (2006.01)
(52) U.S. Cl. ...................... 540/227; 540/226
(58) Field of Classification Search ...................... None
See application file for complete search history.

(56) References Cited

U.S. PATENT DOCUMENTS

| | | | |
|---|---|---|---|
| 4,767,852 A | 8/1988 | Ascher | |
| 4,839,350 A | 6/1989 | Atsumi et al. | |
| 5,616,703 A | 4/1997 | Ludescher et al. | |
| 6,235,897 B1 | 5/2001 | Ludescher et al. | |
| 6,288,223 B1 * | 9/2001 | Okada et al. | 540/220 |
| 6,288,233 B1 | 9/2001 | Kuo et al. | |
| 2003/0225265 A1 | 12/2003 | Deshpande et al. | |
| 2008/0033166 A1 * | 2/2008 | Nishioka et al. | 540/226 |

FOREIGN PATENT DOCUMENTS

| | | |
|---|---|---|
| EP | 1 016 665 A1 | 7/2000 |
| EP | 1752460 A1 * | 2/2007 |
| WO | WO 03/099826 A1 | 12/2003 |
| WO | WO 2005/016936 A2 | 2/2005 |
| WO | WO 2005/044824 A2 | 5/2005 |
| WO | WO 2005/100367 A1 | 10/2005 |
| WO | WO 2005/100369 A1 | 10/2005 |

OTHER PUBLICATIONS

Sakagami et al., "Synthesis and Oral Activity of Pivaloyloxymethyl 7-[(Z)-2-(2-Aminothiazol-4-yl)-2-methoxyiminoaceta-mido]-3(Z)-(4-methylthiazol-5-yl)vinyl-3-cephem-4-carboxylate (ME1207) and Its Related Compound," Chem. Pharm. Bull. vol. 39, No. 9, pp. 2433-2436, 1991.
Jung, Myung Hee et al., "Synthesis and Antibacterial activity of C-3-(substituted vinyl cephalosporins. VI," Korean Journal of Medicinal Chemistry, Korean Chemical Society, Seoul, KR, vol. 8, No. 2, pp. 92-95, 1998.

* cited by examiner

*Primary Examiner*—Mark L Berch
(74) *Attorney, Agent, or Firm*—Oliff & Berridge, PLC

(57) ABSTRACT

The present invention relates to an improved process for the preparation of Cefditoren of formula (I), the said process comprising the steps of: i) converting the compound of formula (II) to a compound of the formula (III) using TPP and sodium iodide in the presence of THF, water, and base; ii) reacting the compound of formula (III) with 4-methyl-5-formyl-thiazole to produce a compound of formula (IV); iii) deesterifying the compound of the formula (IV) to yield compound of formula (V); iv) converting the compound of formula (V) to compound of formula (VI) in the presence of a base and solvent; v) converting the compound of formula (VI) into compound of formula (VII) by enzymatic hydrolysis; and vi) reacting compound of formula (VII) with compound of formula (VIII) in the presence of solvent and base to produce compound of formula (I).

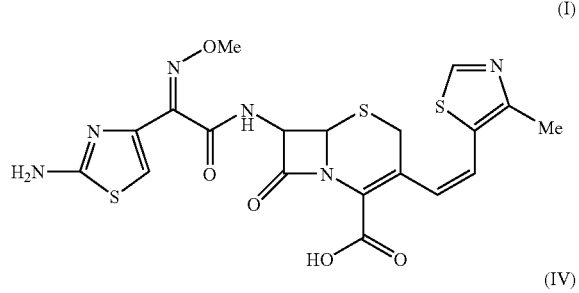

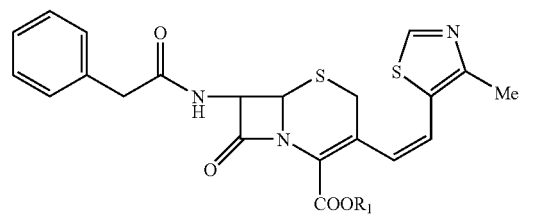

14 Claims, No Drawings

PROCESS FOR THE PREPARATION OF CEFDITOREN

FIELD OF THE INVENTION

The present invention relates to a process for the preparation of 7-α-aminoacyl-cephalosporin of formula (I). More particularly, the present invention relates to a process for the preparation of {(6R,7R)-7-[(Z)-2-(2-Aminothiazol-4-yl)-2-(methoxyimino)acetamido]-3-[(Z)-2-(4-methylthiazol-5-yl)ethenyl]-3-cephem-4-carboxylic acid} Cefditoren of the formula (I) or its pharmaceutically acceptable salts or esters.

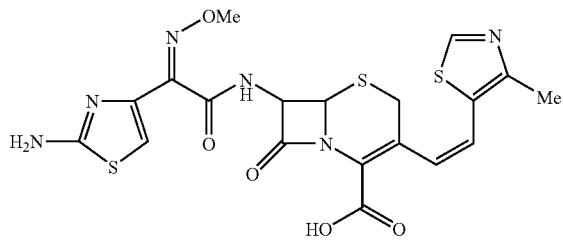

BACKGROUND OF THE INVENTION

Cefditoren has low toxicity to mammals but exhibits a very broad antibacterial spectrum against positive-bacteria and gram-negative bacteria. Cefditoren is known to be a highly excellent therapeutic agent, which has been extensively utilized for the therapeutic treatments and preventive treatments of bacterial infections caused, by a variety of gram-positive bacteria and gram-negative bacteria.

Originally Cefditoren was disclosed in U.S. Pat. No. 4,839,350. This patent also discloses various processes for the preparation of Cefditoren.

U.S. Pat. Nos. 5,616,703 and 6,235,897 discloses a process for the depletion of 7-amino-3-[(E)-2-(4-methyl-5-thiazolyl)vinyl]-3-cephem-4-carboxylic acid in Z/E mixtures of 7-amino-3-[2-(4-methyl-5-thiazolyl)vinyl]-3-cephem-4-carboxylic acid a) by subjecting an amine salt of a Z/E mixture of 7-amino-3-[2-(4-methyl-5-thiazolyl)vinyl]-3-cephem-4-carboxylic acid to crystallization and converting this amine salt into 7-amino-3-[2-(4-methyl-5-thiazolyl)vinyl]-3-cephem-4-carboxylic acid, or b) by subjecting the Z/E mixture to chromatography.

U.S. Pat. No. 6,288,233 discloses a process for the preparation of Cefditoren by condensing Wittig salt of cephem moiety with thiazole-5-carbaldehyde in a mixture of chlorinated hydrocarbon and lower alkanol medium.

Chem. Pharm. Bull. 39, (1991), 2433 discloses a process which involves conversion of GCLE (II) into Wittig salt, Wittig reaction with 5-formyl-4-methylthiazole, separation of isomer by fractional crystallization followed by column chromatography, deprotection to get free amine, reaction with protected MAEM followed by deprotection to get free acid (I). The E/Z isomer separation involves column chromatography hence yield is less.

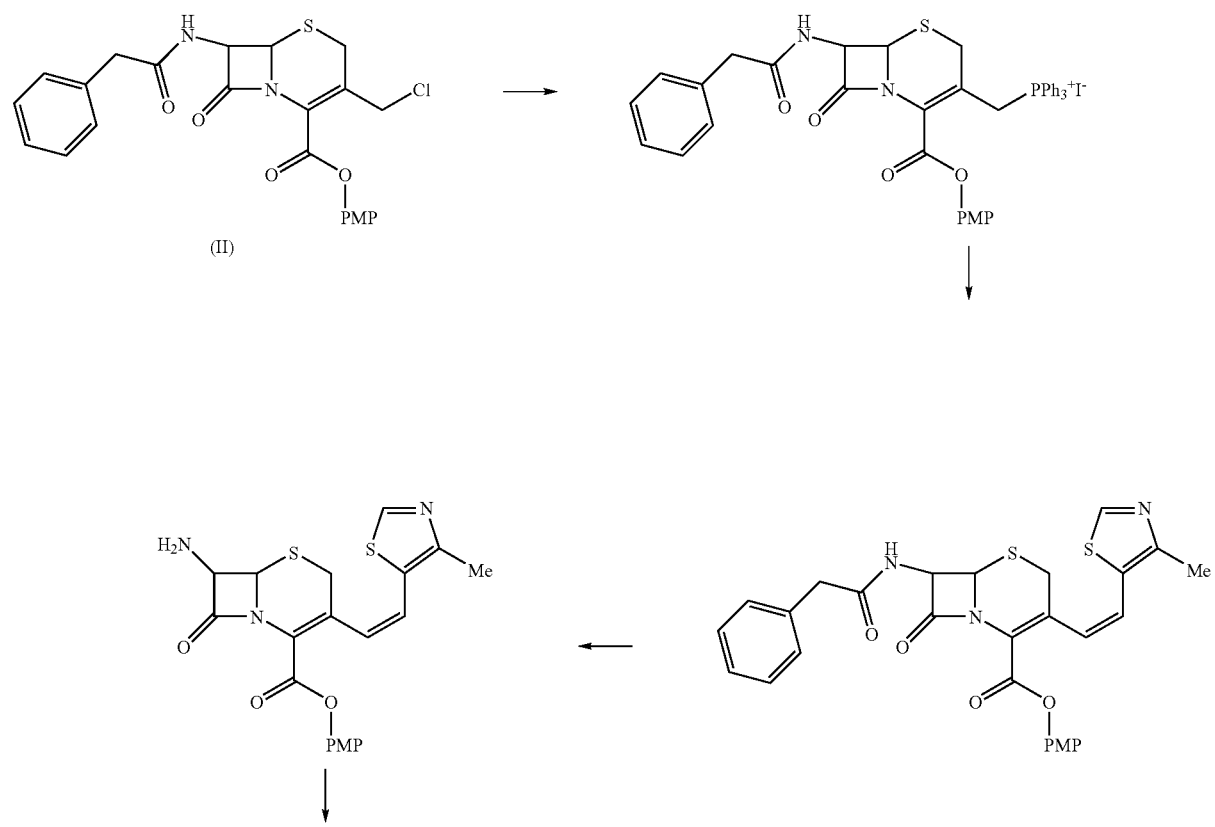

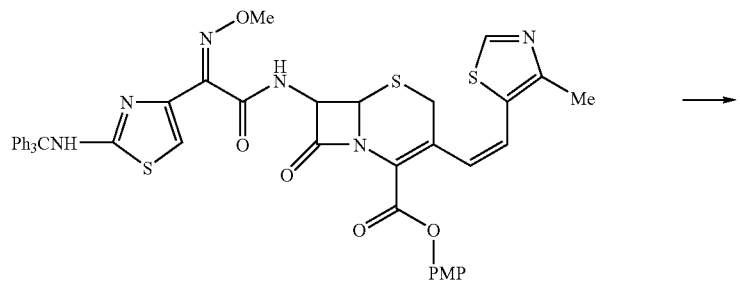

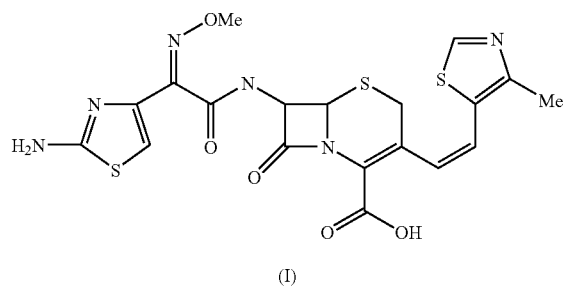

wherein PMP denotes p-methoxy phenyl

The foregoing processes are associated with many problems such as poor yield and quality, difficult to commercialization, impurity and percentage of E isomer content is high. Hence there is a need to develop a process, which is easy to commercialize, and which yields good quality as well as quantity. We focused our research to find a process and finally achieved identifying a clean process for producing the title compound of the invention, which contains less percentage of E isomer.

OBJECTIVE OF THE INVENTION

The main objective of the present invention is to provide a process for the preparation of 7-α-aminoacyl-cephalosporin derivatives of the general formula (I), which contains less percentage of E isomer.

Another objective of the present invention is to provide a stable process for the preparation of Cefditoren, which is easy to commercialize.

Another objective of the present invention is to provide a high yielding process with good quality.

SUMMARY OF THE INVENTION

Accordingly, the present invention provides a process for the preparation (6R,7R)-7-[2-amino-4-thiazolyl[(methoxy-imino)acetyl]amino]-3-[2-(4-methyl-5-thiazolyl)vinyl-3-cephem-4-carboxylic acid derivatives of the formula (I)

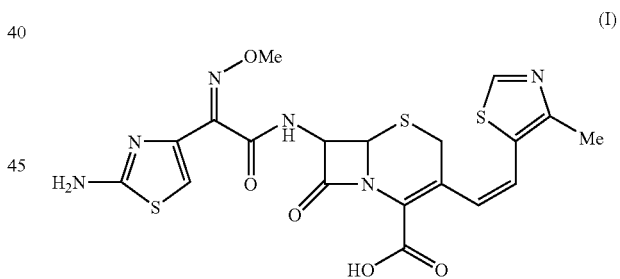

The said comprising the steps of:
i) converting the compound of formula (II) wherein $R_1$ represents carboxy protecting group to a wittig ylide of formula (III) using wittig reagent and alkali iodide in the presence of aprotic solvent, water and base,
ii) reacting the compound of formula (III) with 4-methyl-5-formyl-thiazole in the presence of aprotic solvent, water and a base to produce a compound of formula (IV) wherein $R_1$ is as defined above,
ii) reacting the compound of formula (III) with 4-methyl-5-formyl-thiazole in the presence of aprotic solvent, water and a base to produce a compound of formula (IV) wherein $R_1$ is as defined above,
iii) deesterifying the carboxy protecting group of compound of the formula (IV) using an acid in the presence of solvent to yield compound of formula (V), iv) converting the compound of formula (V) to compound of formula (VI) wherein X represents a counter ion which forms a salt in the presence of a base and solvent,
v) converting the compound of formula (VI) into compound of formula (VII) by enzymatic hydrolysis, and
vi) reacting compound of formula (VII) or its reactive derivative with compound of formula (VIII) wherein Y is a group which forms a basis that a compound of formula (VII) is in a reactive form; including halogen, a group which forms together with the —C═O group to which Y is attached an active thioester, and a group which forms together with the —C═O group to which Y is attached a mixed anhydride in the presence of solvent and in presence or absence of base to produce compound of formula (I).

The process is shown in Scheme-2

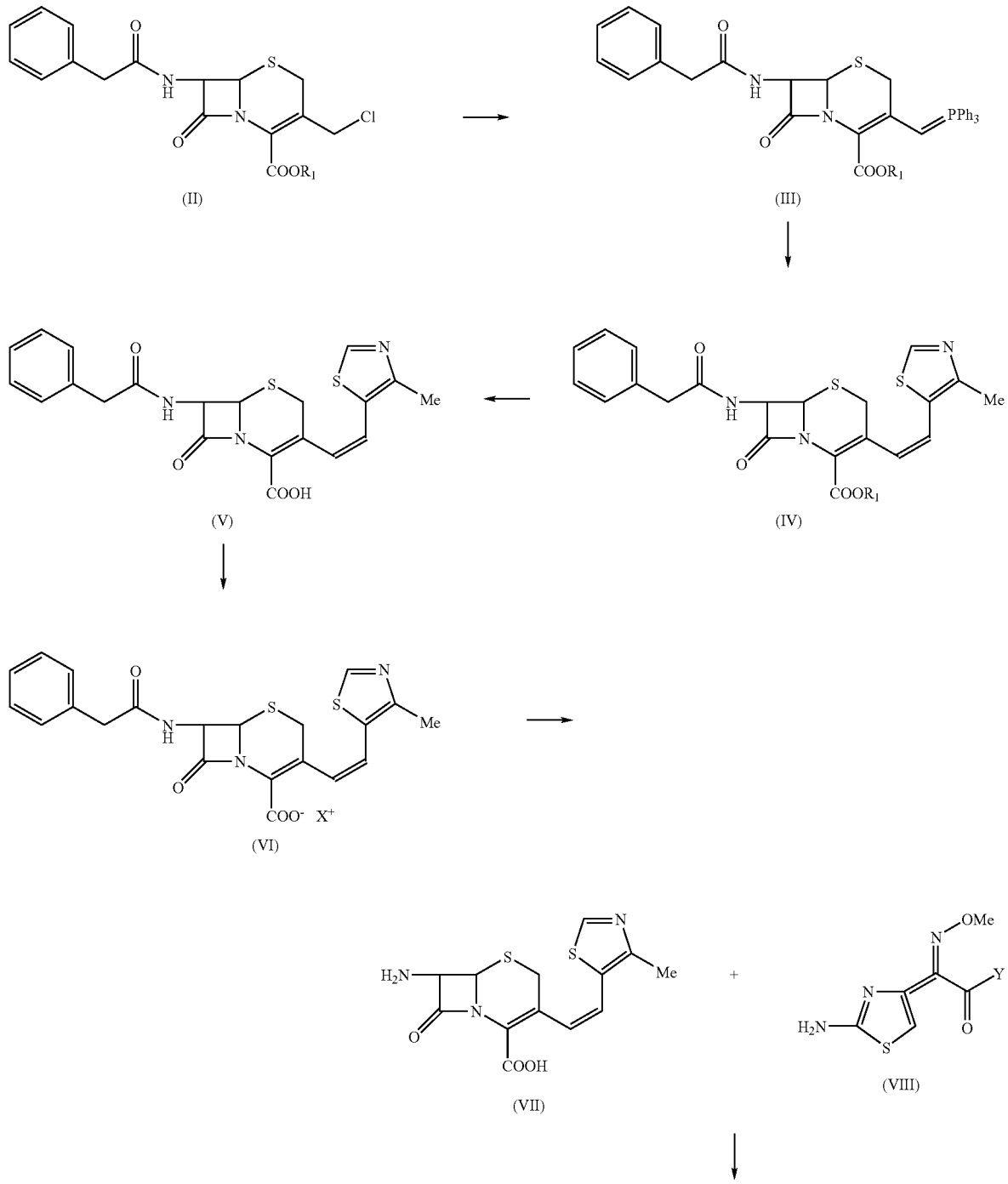

-continued

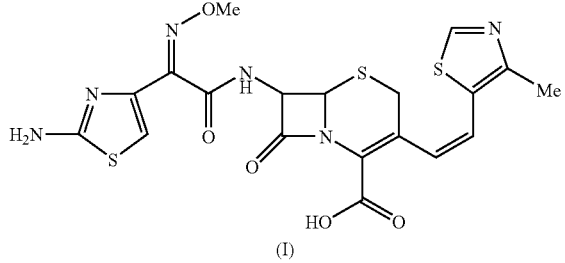

(I)

DETAILED DESCRIPTION OF THE INVENTION

In an embodiment of the present invention, the carboxy protecting group represented by $R^1$ is selected from $(C_1-C_6)$ alkyl group such as methyl, ethyl, propyl, isopropyl, t-butyl and the like; p-methoxybenzyl, p-nitrobenzyl, o-chlorobenzyl, diphenylmethyl and the like.

In yet another embodiment of the present invention the aprotic solvent used in step (i) and (ii) is selected from methylene chloride, ethylene dichloride, acetone, THF, acetonitrile, ethyl methyl ketone, methyl isobutyl ketone, toluene, IPE, hexane, ethyl acetate, hexamethyl phosphoramide, diglyme, monoglyme, ethylene glycol, DMF, DMAc, and the like or mixtures thereof.

In still another embodiment of the present invention the percentage of required isomer (Z) is more when the mixture of THF and water employed in step (i & ii).

In yet another embodiment of the present invention the wittig reagent employed is selected from TPP, triphenylphosphine; and alkali iodide employed is selected from sodium iodide, potassium iodide.

In an embodiment of the present invention, the base employed in step (i) and (ii) alkali/alkaline earth metal bicarbonates like sodium bicarbonate, potassium bicarbonate, alkali/alkaline earth metal carbonates like sodium carbonate, potassium carbonate alkali/alkaline earth metal hydroxides like sodium hydroxide, potassium hydroxide.

In yet another embodiment of the present invention the deesterification in step (iii) is carried out using phenol/trifluoroacetic acid, anisole/trifluoroacetic acid, formic acid, PTSA, hydrochloric acid, $AlCl_3$, using solvent such as halogenated hydrocarbon like MDC, EDC; esters like ethyl acetate, n-butyl acetate; alkanols like methanol, iso-propanol; N,N dimethyl aniline, water and the like or mixture thereof.

In yet another embodiment of the present invention the conversion in step (iv) is carried out in the presence of solvent selected from water, acetone, DMF, THF, DMAc, DMSO, halogenated alkanes and the like using base such as sodium hydroxide, lithium hydroxide, potassium hydroxide, ammonia, alkali/alkaline earth metal bicarbonates like sodium bicarbonate, potassium bicarbonate, alkali/alkaline earth metal carbonates like calcium carbonate, sodium carbonate, potassium carbonate, or organic base such as tertiary butyl amine, benzyl amine, dibenzyl amine, diethyl amine, diisopropyl amine, dicyclohexyl amine, benzathine, octyl amine, dicyclohexyl diethanolamine and the like.

In one more embodiment of the present invention, the invention can be performed without carrying out the step (iv).

The still another embodiment of the present invention, the enzyme used is selected from penicillin G amidase (PGA).

In yet another embodiment of the present invention the solvent used in step (vi) is selected from cyclohexane, methylene chloride, ethylene dichloride, acetone, THF, acetonitrile, ethyl methyl ketone, methyl isobutyl ketone, toluene, IPE, hexane, ethyl acetate, water, ethylene glycol, DMF, DMAc, methanol or mixtures thereof.

In another embodiment of the present invention the reactive derivative of compound of formula (VII) includes silylated derivative, or salts with bases such as TMG, TEA, DCHA, benzathine, octyl amine, sodium or potassium salt, and the like.

In still another embodiment of the present invention compound of formula (VII) may contain some amount of (E)-isomer.

In yet another embodiment of the present invention the reactive derivative of compound of formula (VIII) includes acid halide like acid chloride; acid anhydride by using ethyl chloro formate or pivaloyl chloride; active amide, thioester like MAEM; and the like.

In another embodiment of the present invention the reaction of compound of formula (VII) with compound of formula (VIII) can be carried out by the method disclosed in our own Indian patent application number 389/MAS/2002

In yet another embodiment of the present invention the reaction of compound of formula (VII) with compound of formula (VIII) can be carried out if required in the presence of base.

The advantages of the present process are that the reaction can be carried out if required without isolating the product at any stage (i.e. reaction can be carried out in situ manner), which is very useful in commercial scales.

In one more embodiment of the present invention the compound of formula (I) obtained can be converted into pharmaceutically acceptable salts like sodium salt or esters like Pivoxil.

The foregoing technique has been found to be markedly attractive, both from commercial point of view, as well as from manufacturing point of view, and affords good quality of Cefditoren of the formula (I).

Many other beneficial results can be obtained by applying disclosed invention in a different manner or by modifying the invention with the scope of disclosure.

The present invention is illustrated with the following example, which should not be construed as limiting the scope of the invention.

EXAMPLE 1

Preparation of p-Methoxybenzyl 7-phenylacetamido-3-(4-methylthiazol-5-yl)vinyl-3-cephem-4-carboxylate To a mixture of tetrahydrofuran (1 lit) and DM Water (1 lit.) at about 30° C. were added, GCLE (200 g), Sodium iodide (6.17 g) and TPP (110 g). The reaction mixture was stirred till the reaction was complete. To the phosphonium salt thus formed, sodium bicarbonate (41.5 g) and 4-Methyl-5-formyl-1,3-thiazole (78.4 g) were added and stirred at 25° till completion of the reaction. The reaction was worked up by adding MDC and water followed by separating the layers. The organic layer was washed with 10% sodium metabisulphite solution and concentrated under reduced pressure at 25° C. to get residue.

Preparation of 7-Amino-3-(4-methylthiazol-5-yl) vinyl-3-cephem-4-carboxylic acid To the p-Methoxybenzyl 7-phenylacetamido-3-(4-methylthiazol-5-yl)vinyl-3-cephem-4-carboxylate obtained from the above step phenol and trifluoro acetic acid (100 ml) were charged at 45° C. The reaction was stirred till completion of reaction. After completion of the reaction, n-butyl acetate and water wer; added to the reaction, stirred and layers were separated. To the organic layer, 5% sodium bicarbonate solution (2 lit.) was added, and stirred for 1 hour and the layers were separated. The aqueous layer was washed with n-butyl acetate and then charcoalised with 10% carbon. Carbon was filtered and to the aqueous layer (containing 7-phenylacetamido-3-(4-methylthiazol-5-yl)vinyl-3-cephem-4-carboxylic acid) was charged Pen G amidase (200 g) and stirred at 25-30° C. while maintaining pH at 7.5-8.5 with aqueous ammonia till completion of reaction after which, the enzyme was filtered and washed with water. The pH of the clear filtrate was adjusted to 3.0 with 1:1 HCl at 10° C. The precipitated solid was filtered and washed with water and ethyl acetate to yield the title compound. {Purity (HPLC): 90-95% weight: 60 gm (on dry basis)}

Preparation of Cefditoren Acid

To a mixture of THF (300 ml) and DM Water (300 ml), were added 7-Amino-3-(4-methylthiazol-5-yl)vinyl-3-cephem-4-carboxylic acid (60 g) and MAEM (78 g) and the reaction mixture was stirred at 15°-20° C. while maintaining the pH at 7.0-7.5 using TEA till the reaction was complete. After completion of reaction, the reaction mass was poured into a mixture of DM Water and Ethyl Acetate. The reaction mixture was stirred and layers were separated. The aqueous layer was washed with ethyl acetate, charcoalised; filtered and then the pH of the filtrate was adjusted to 2.5-3.0 with 1:1 HCl at 10° C. The solid obtained was filtered and washed with DM water and then with MDC to yield Cefditoren acid.

Preparation of Cefditoren Sodium

To a mixture of DM Water (80 ml) Acetone (160 ml), was added cefditoren acid (20 g on dry basis) and stirred to get a clear solution. The clear solution was charcolized and filtered. To the clear filtrate, Sodium-2-Ethyl hexanoate (13.2 g) was added at 30°. To the reaction mixture was added acetone (400 ml) and stirred. The precipitated solid was filtered, washed with acetone dried under vacuum to get Cefditoren Sodium.

Preparation of Cefditoren Pivoxil

To DMF (80 ml), Cefditoren Sodium (10 gm) was added at 30° C. and stirred to get a clear solution. To the clear solution, solid sodium bicarbonate (1.6 gm), and tetra butyl ammonium hydrogen sulphate were added. The reaction mass was cooled to −20° C. and iodomethyl pivalate (9.76 gm) was charged and stirred for 60 minutes. The reaction mass was poured into isopropyl ether (100 ml). To this reaction mixture DM Water (100 ml) was added. The solid obtained was stirred at 5° C., filtered, washed with water and IPE, and finally dried to get the title compound. Purity(HPLC): 97-99% Yield: 8.5 gm.

[Iodomethyl pivalate may be prepared as follows:
Chloromethyl pivalate (20 g) and sodium iodide (30 gm) were added to acetone (100 ml) at 15° C. The reaction mass was stirred for 6.0 hours at 25° C. and then poured into a pre-cooled mixture of MDC and DM Water; stirred for 10 minutes and layers separated. The organic layer was washed with 100 ml of 5% sodium thiosulphate solution and subsequently concentrated at reduced pressure to get iodomethylpivalate as a pale yellow liquid.]

Abbreviations:
GCLE: p-Methoxybenzyl 7-phenylacetamido-3-chloromethy-3-cephem-4-carboxylate
MDC: Dichloromethane
TPP: Triphenylphosphine
MAEM: 2-(2-aminothiazol-4-yl)-2-syn-methoximino acetic acid 2-benthiazolyl thioester
DMF: Dimethyl formamide
DMAc: Dimethyl acetamide
IPE: Isopropyl ether
DM water: Demineralised water
DMSO: Dimethyl sulfoxide
EDC: Ethylene dichloride
PTSA: p-toluene sulfonic acid

We claim:
1. A process for the preparation of Cefditoren of formula (I) or its ester or pharmaceutically acceptable salts there of

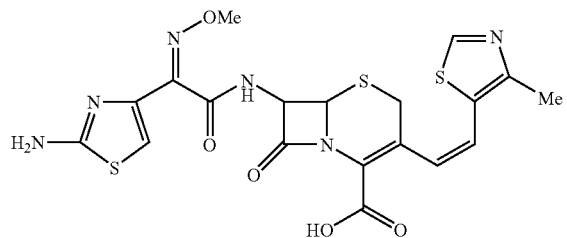

(I)

which comprising the steps of:
i) converting the compound of formula (II)

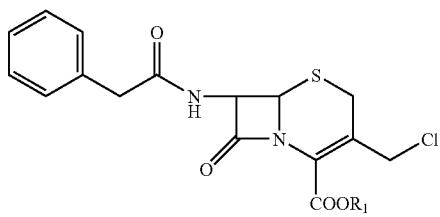

(II)

wherein $R_1$ represents carboxy protecting group to a compound of the formula (III)

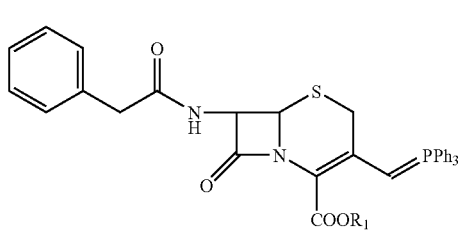

(III)

using triphenylphosphine and alkali iodide in the presence of aprotic solvent, water and base, ii) reacting the compound of formula (III) with 4-methyl-5-formyl-thiazole in the presence of aprotic solvent, water and base to produce a compound of formula (IV)

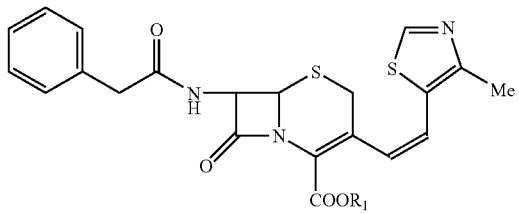

(IV)

wherein $R_1$ is as defined above, iii) deesterifying the carboxy protecting group of compound of the formula (IV) using an acid in the presence of solvent to yield compound of formula (V),

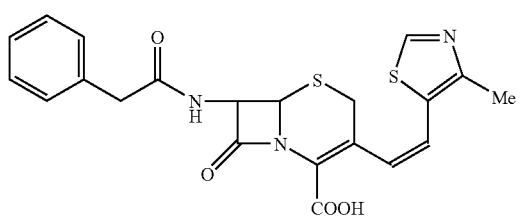

(V)

iv) converting the compound of formula (V) to compound of formula (VI)

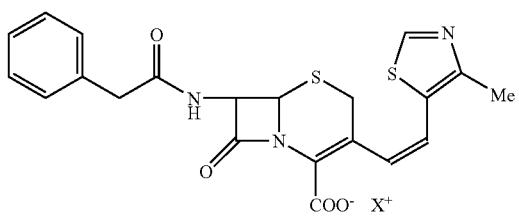

(VI)

wherein X represents a counter ion which forms a salt; in the presence of a base and solvent, v) converting the compound of formula (VI) into compound of formula (VII)

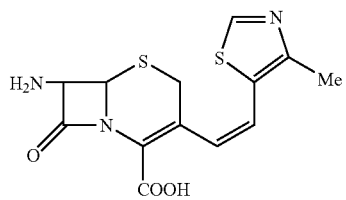

(VII)

by enzymatic hydrolysis, and vi) reacting compound of formula (VIII) with compound of formula (VII)

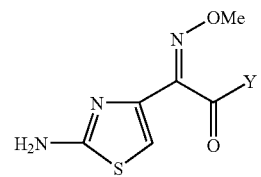

(VIII)

wherein Y is selected from halogen, and 2-mercaptobenzothiazole (MBT), and in the presence of solvent and in presence or absence of base to produce compound of formula (I).

2. The process as claimed in claim 1, wherein the carboxy protecting group represented by $R^1$ is selected from a ($C_1$-$C_6$) alkyl group, p-methoxybenzyl, p-nitrobenzyl, o-chlorobenzyl, or diphenylmethyl.

3. The process as claimed in claim 1, the solvent used in step (i) and step (ii) is selected from methylene chloride, ethylene dichloride, acetone, THF, acetonitrile, ethyl methyl ketone, methyl isobutyl ketone, toluene, IPE, hexane, ethyl acetate, hexamethyl phosphoramide, diglyme, monoglyme, 1,4 dioxan, ethylene glycol, DMF, DMAc, trihexyl(tetradecyl)phosphonium hexa fluorophosphate, trihexyl(tetradecyl) phosphonium tetrafluorophosphate; or mixtures thereof.

4. The process as claimed in claim 1, wherein the solvent used in step (i) & (ii) is selected form mixture of THF and water.

5. The process as claimed in claim 1, wherein the base used in step (i & ii) is selected from sodium bicarbonate, potassium bicarbonate, sodium carbonate, sodium hydroxide, potassium hydroxide, or potassium carbonate.

6. The process as claimed in claim 1, wherein the desertification in step (iii) is carried out using phenol/trifluoroacetic acid, anisole/trifluoroacetic acid, formic acid, PTSA, hydrochloric acid; and the solvent used is selected from MDC, EDC, ethyl acetate, n-butyl acetate, methanol, iso-propanol; water and the like or mixture thereof.

7. The process as claimed in claim 1, wherein the solvent used in step (iv) is selected from water, acetone, DMF, THF, DMAc, DMSO, MDC, EDC, or methanol; and the base employed is sodium hydroxide, lithium hydroxide, potassium hydroxide, ammonia, sodium bicarbonate, potassium bicarbonate, sodium carbonate, potassium carbonate, tertiary butyl amine, benzyl amine, dibenzyl amine, triethylamine, diethyl amine, diisopropyl amine, dicyclohexyl amine, octyl amine, or dicyclohexyl diethanolamine.

8. The process as claimed in claim 1, wherein the enzyme used in step (v) is selected from penicillin G amidase (PGA).

9. The process as claimed in claim 1, wherein the solvent used in step (iv) is selected from methylene chloride, ethylene dichloride, acetone, THF, acetonitrile, ethyl methyl ketone, methyl isobutyl ketone, toluene, IPE, hexane, ethyl acetate, water, ethylene glycol, DMF, DMAc, methanol, cyclohexane or mixtures thereof.

10. A process for the preparation of Cefditoren or its ester or pharmaceutically acceptable salts there of, which comprising the steps of:

i) converting the compound of formula (II)

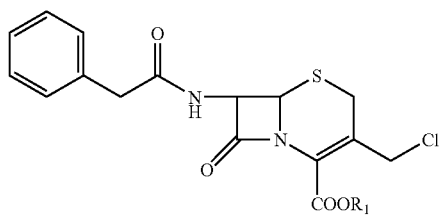

(II)

wherein R₁ represents carboxy protecting group to a compound of the formula (III)

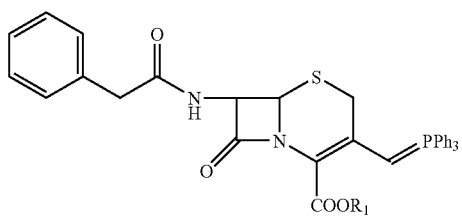

(III)

using TPP and sodium iodide in the presence of THF, water, and base, ii) reacting the compound of formula (III) with 4-methyl-5-formyl-thiazole in the presence of THF, water and base to produce a compound of formula (IV)

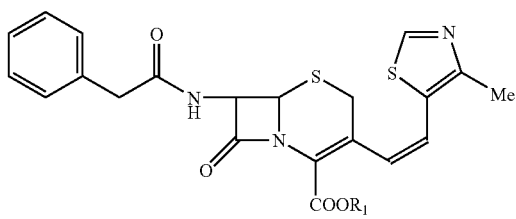

(IV)

wherein R₁ is as defined above, iii) deesterifying the carboxy protecting group of compound of the formula (IV) using phenol/trifluoroacetic acid in the presence of solvent to yield compound of formula (V),

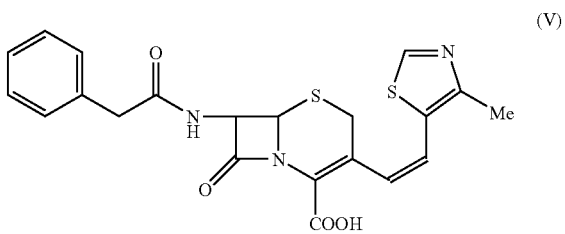

(V)

iv) converting the compound of formula (V) to compound of formula (VI)

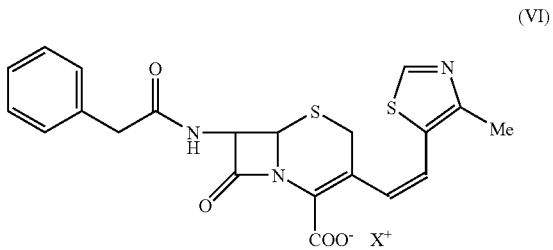

(VI)

wherein X represents a counter ion which forms a salt in the presence of a base and solvent, v) converting the compound of formula (VI) into compound of formula (VII)

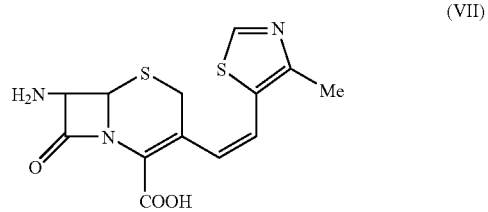

(VII)

by enzymatic hydrolysis, and vii) reacting compound of formula (VIII) with compound of formula (VII)

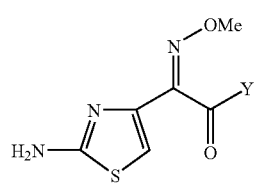

(VIII)

where in Y is as defined above
in the presence of solvent and base to produce compound of formula (I).

11. The process according to claim 1, further comprising converting the compound of formula (I) to its pharmaceutically acceptable salt or ester by conventional methods.

12. The process as claimed in claim 3, wherein the solvent used in step (i) & (ii) is selected form mixture of THF and water.

13. The process according to claim 10, further comprising converting the compound of formula (I) to its pharmaceutically acceptable salt or ester by conventional methods.

14. The process as claimed in claim 2, wherein the $(C_1-C_6)$ alkyl group is selected from the group consisting of methyl, ethyl, propyl, isopropyl and t-butyl.

* * * * *